United States Patent
Jonkman

(10) Patent No.: US 6,264,645 B1
(45) Date of Patent: Jul. 24, 2001

(54) METHOD OF PRESSURIZING THE RIGHT VENTRICLE OF THE HEART

(75) Inventor: Kenneth R. Jonkman, Grand Rapids, MI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/247,415

(22) Filed: Feb. 10, 1999

Related U.S. Application Data

(63) Continuation-in-part of application No. 09/012,521, filed on Jan. 23, 1998, now Pat. No. 6,059,760, which is a continuation-in-part of application No. 08/911,334, filed on Aug. 14, 1997, now Pat. No. 5,858,009.

(51) Int. Cl.[7] .................................................. A61M 31/00
(52) U.S. Cl. ........................................... 604/508; 604/532
(58) Field of Search ................................... 604/500, 507, 604/508, 509, 264, 532, 534, 537, 39, 43

(56) References Cited

U.S. PATENT DOCUMENTS

| | | |
|---|---|---|
| 3,734,083 | 5/1973 | Kolin . |
| 4,129,129 | 12/1978 | Amrine . |
| 4,451,252 | 5/1984 | Martin . |
| 4,543,087 | 9/1985 | Sommercorn et al. . |
| 4,675,004 | 6/1987 | Hadford et al. . |
| 4,795,439 | 1/1989 | Guest . |
| 4,846,806 | 7/1989 | Wigness et al. . |
| 5,160,325 | 11/1992 | Nichols et al. . |
| 5,348,536 | 9/1994 | Young et al. . |
| 5,374,245 | 12/1994 | Mahurkar . |
| 5,451,206 | 9/1995 | Young . |
| 5,554,136 | 9/1996 | Luther . |
| 5,556,390 | 9/1996 | Hicks . |
| 5,569,182 | 10/1996 | Twardowski et al. . |

*Primary Examiner*—Anhtuan T. Nguyen
(74) *Attorney, Agent, or Firm*—Foley & Lardner

(57) ABSTRACT

A method of pressurizing the right ventricle of the heart. The method includes providing a multi-lumen cannula. The multi-lumen cannula includes a first sub-cannula and a second sub-cannula. The first sub-cannula includes a proximal end, a distal end, a lumen extending between the proximal and distal ends, and proximal and distal fluid apertures formed in the lumen. The second sub-cannula includes a proximal end, a distal end, a lumen extending between the proximal and distal ends, and proximal and distal fluid apertures formed in the lumen. The distal fluid apertures of the two lumens are spaced from one another along the axial length of the multi-lumen cannula. The method further includes inserting the cannula into the vasculature system of a patient so that the distal fluid aperture of the lumen of the second sub-cannula is received in one of the right atrium, the superior vena cava, and the inferior vena cava. The distal fluid aperture of the lumen of the first sub-cannula is received in the right ventricle. The method of pressurizing the right ventricle still further includes fluidly connecting the proximal fluid apertures of the first and second sub-cannulas to a fluid conducting pump for moving fluid through the two sub-cannulas.

21 Claims, 12 Drawing Sheets

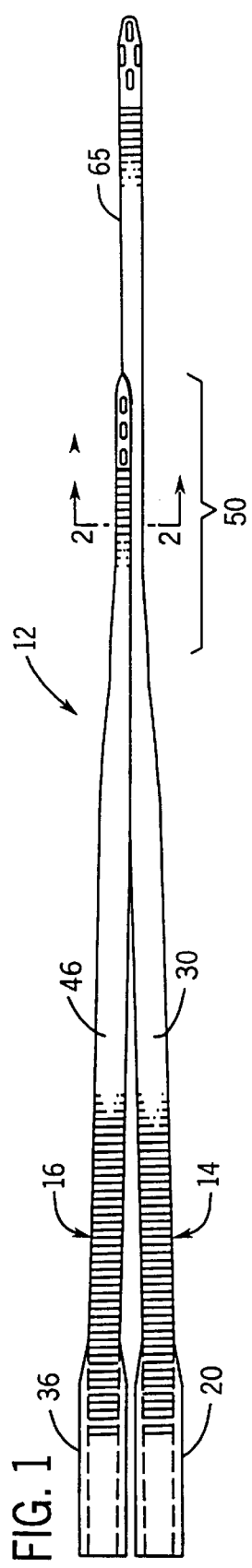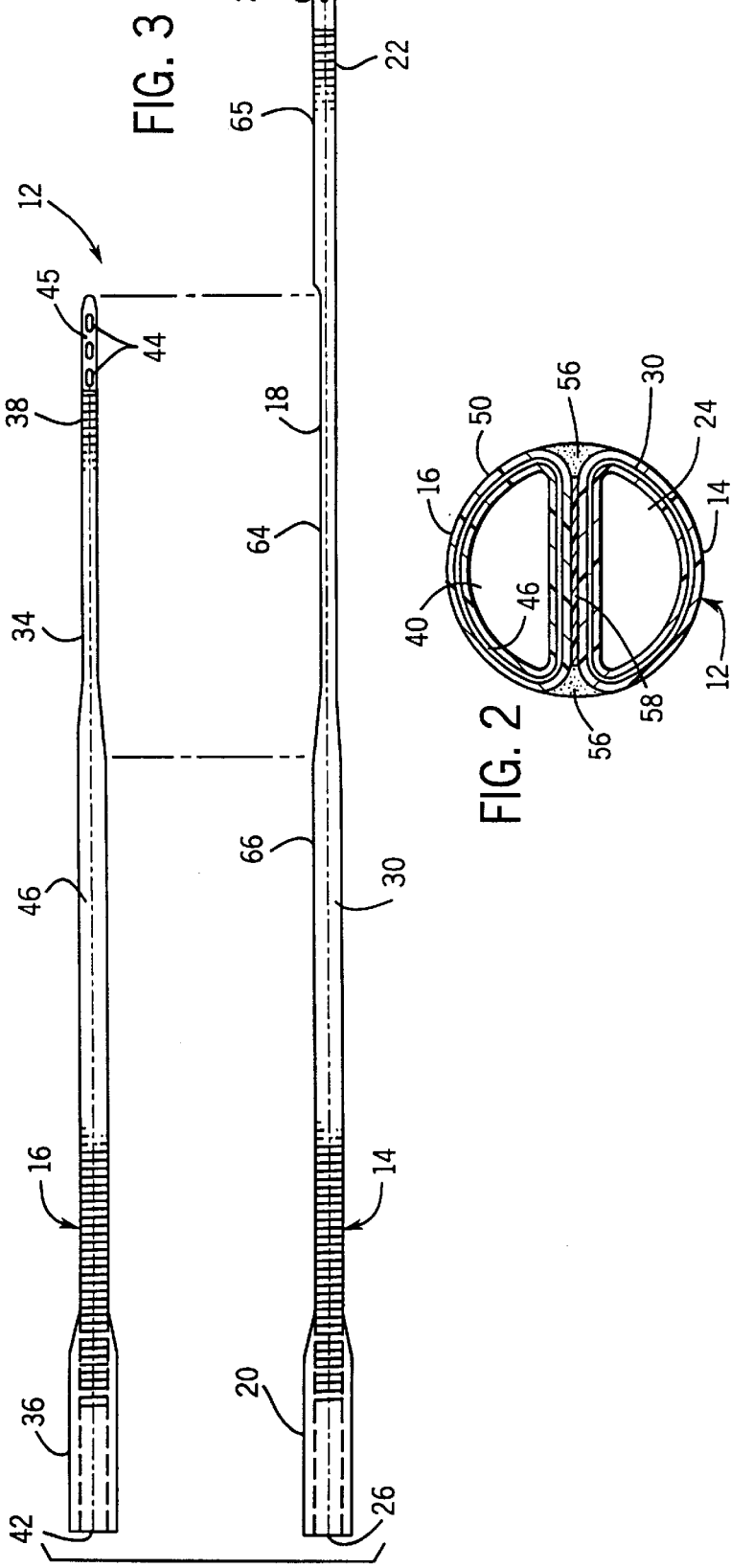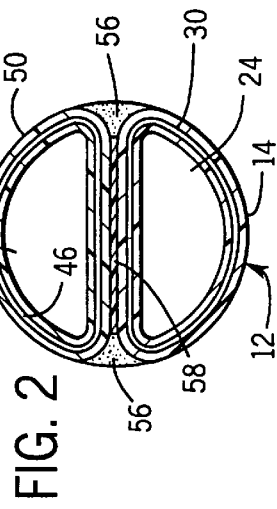

METHOD OF PRESSURIZING THE RIGHT VENTRICLE OF THE HEART

CROSS-REFERENCE TO RELATED APPLICATION

The present application is a continuation-in-part of U.S. patent application Ser. No. 09/012,521, filed on Jan. 23, 1998, now U.S. Pat. No. 6,059,760 which is a continuation-in-part of Ser. No. 08/911,334 issued U.S. Pat. No. 5,858,009 filed on Aug. 14, 1997 and issued on Jan. 12, 1999.

BACKGROUND OF THE INVENTION

1. Field of the Invention

This invention relates to single- and multi-lumen cannulas and, more particularly, to a reinforced cannula having staggered lumen fluid outlets spaced along the length of the cannula and adapted to redirect the flow of fluid, making the cannula ideally suited for use in a variety of cardiac surgical procedures.

2. Description of the Related Art

Cannulas have long been used in a variety of applications to inject or withdraw fluid from the body. It is known to create a single-lumen cannula having wire reinforcement integrated in the body of the cannula to provide enhanced rigidity and avoid kinking of the cannula. It is also known to create a cannula having multiple lumens provided therein for delivering a variety of fluids and medications into and out of the body. However, one significant problem which exists in the art is the creation of a single cannula having multiple lumens formed therein wherein each lumen is independently reinforced so that the cannula can accommodate dramatically different fluid pressures in the adjacent cannulas without risk of collapsing the septum separating the different lumens.

Cannulas are often used in cardiac surgical procedures to conduct fluid to and from the various chambers of the heart and vessels conducting fluid to and from the heart. One desirable goal of a cardiac surgical procedure is to minimize the number of incisions which are formed in the heart and the vessels leading to and from the heart. It is especially important to minimize the number of incisions in the aorta in view of the significant fluid pressures which are experienced by this vessel during normal beating of the heart.

Another desirable goal is to minimize trauma to the heart and vessels leading to and from the heart. Pressurized fluid flowing through the cannula typically exits the cannula at a high velocity and may damage the heart, vessels or valves. In addition, the fluid flow may dislodge plaque from the walls surrounding the cannula, increasing the risk of embolic complications. Accordingly, it is important to reduce trauma to the body during a cardiac surgical procedure.

SUMMARY OF THE INVENTION

The cannula according to the invention overcomes the problems of the prior art by providing a multi-lumen cannula with independently reinforced lumens so that dramatically different fluid pressures can be accommodated in the same multi-lumen cannula. In addition, the cannula according to the invention achieves some of the desirable goals of cardiac surgery by minimizing the number of incisions which must be created in the heart and vessels leading to and from the heart as well as by reducing trauma to the body through redirection of the fluid flow as it exits the cannula.

In accordance with one embodiment of the invention, a cannula for conducting fluid to a body is provided. The cannula includes a cannula body and a cannula tip. The cannula body has proximal and distal ends, and a lumen extending therebetween. The lumen is adapted to receive the fluid flowing therethrough. The cannula tip is coupled to the distal end of the cannula body and includes a side wall having a plurality of fluid outlets formed therein. Each fluid outlet is directed toward the proximal end of the cannula body to reverse the flow of fluid exiting the cannula by an obtuse angle from the original direction of flow.

In another embodiment of the invention, a multi-lumen cannula assembly includes first and second sub-cannulas. Each sub-cannula has proximal and distal ends, and a lumen extending therebetween. The second sub-cannula is adhered to a portion of the first sub-cannula to create a septum separating the lumens of the first and second sub-cannulas. The first sub-cannula also includes a reinforcement to resist radial deflection of the lumen, and a cannula tip, located at the distal end. The cannula tip has a plurality of fluid apertures formed therein. The reinforcement of the first sub-cannula resists deflection of the septum as a result of differing fluid pressure levels inside the lumens. The second sub-cannula, which is adhered to a portion of the first sub-cannula, includes a cannula tip located at a distal end. The cannula tip of the second sub-cannula has a plurality of fluid outlets formed therein, each fluid outlet being directed toward the proximal end of the second sub-cannula. The fluid outlets reverse the flow of fluid exiting the second sub-cannula by an obtuse angle from the original direction of flow.

The invention is also directed to a method of steering a cannula. The method includes the step of providing a cannula including a cannula tip. The cannula tip includes a side wall having at least one fluid outlet formed therein and disposed about a sector of the cannula tip, the sector being less than the entire cannula tip. The method also includes the step of conducting a fluid through the lumen of the cannula. The fluid exits the cannula through the at least one fluid outlet and guides the cannula tip in a direction away from the at least one fluid outlet.

The invention is further directed to a cannula for conducting fluid to a body. The cannula includes a cannula body and a cannula tip coupled to a distal end of the cannula body. The cannula body includes a mid-section having a plurality of fluid outlets formed therein. Each of the plurality of fluid outlets is directed toward a proximal end of the cannula body to reverse the flow of fluid exiting the cannula by an obtuse angle from the original direction of flow.

Other advantages of the invention will become apparent from the detailed description given hereinafter. It should be understood, however, that the detailed description and specific embodiments are given by way of illustration only, since, from this detailed description, various changes and modifications within the spirit and scope of the invention will become apparent to those skilled in the art.

BRIEF DESCRIPTION OF THE DRAWINGS

The preferred exemplary embodiments of the present invention will hereinafter be described in conjunction with the accompanying drawings, wherein like numerals denote like elements and:

FIG. 1 is a top, plan view of a multi-lumen cannula according to the invention;

FIG. 2 is a cross-sectional view of the multi-lumen cannula taken generally along the line 2—2 of FIG. 1;

FIG. 3 is an exploded, top, plan view of the multi-lumen cannula of FIG. 1;

DETAILED DESCRIPTION OF THE PREFERRED EMBODIMENTS

Figure 4:
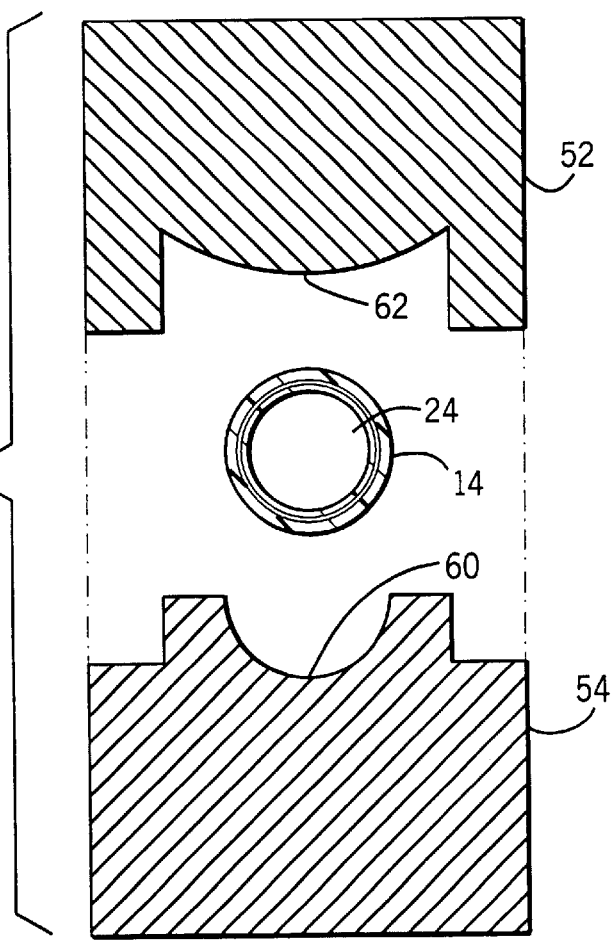
FIG. 4 is a sectional view of a die assembly used in the manufacture of the multi-lumen cannula, the die assembly being adapted to deform the sub-cannula.

Referring now to the drawings and to FIGS. 1–3 in particular, a multi-lumen cannula 12 according to the invention is shown. The multi-lumen cannula 12 comprises a first sub-cannula 14 and a second sub-cannula 16 which are mounted to one another to create the multi-lumen cannula 12. The first sub-cannula 14 comprises a wire reinforced body portion 18 having a proximal end 20 and a distal end 22. A lumen 24 extends from a proximal lumen aperture 26 provided on the proximal end 20 to at least one distal lumen aperture 28 formed in a cannula tip 29 at the distal end 22. The body portion 18 is formed of a flexible material acceptable for use inside the human body, preferably polyvinyl chloride. Preferably, the body portion 18 includes some form of reinforcing to provide radial rigidity to the cannula and to prevent kinking of the cannula during deformation. The preferred means of reinforcement comprises a conventional helical wire 30 imbedded in the body portion 18.

The structural elements of the second sub-cannula 16 are substantially identical to those of the first sub-cannula and include a body portion 34, a proximal end 36, a distal end 38, a lumen 40, a proximal lumen aperture 42, at least one distal lumen aperture 44 formed in a cannula tip 45, and a reinforcing wire 46.

In the preferred embodiment, the first sub-cannula 14 is longer than the second sub-cannula 16, and the second sub-cannula 16 is secured to the first sub-cannula 14 such that the proximal ends 20, 36 are immediately adjacent one another and the distal ends 22, 38 are spaced from one another. Further, the distal end 22 of the second sub-cannula 16 and a portion of the body immediately adjacent the distal end 22 is securely adhered to the body 18 of the first sub-cannula 14. The adhered portion 50 of the two sub-cannulas is dimensioned and designed to avoid any sharp corners or contours and provide a smooth transition along the exterior surface, without adversely affecting the flow rate through the lumens of the two sub-cannulas. These features are achieved by deforming portions of the sub-cannulas utilizing a die similar to that seen in FIGS. 4 and 5.

Figure 5:
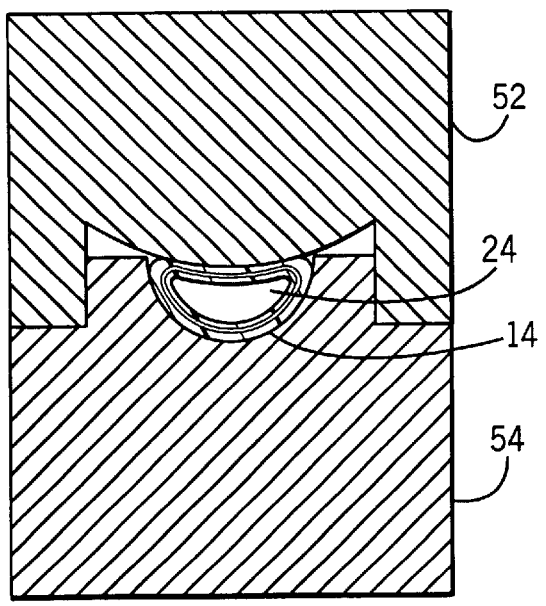
FIG. 5 is a sectional view of the die assembly of FIG. 4 showing the die assembly in the closed position.

The portions of the first and second sub-cannulas 14, 16 which comprise the adhered portion 50 are preferably D-shaped in cross-section and secured to one another so that the flat portions of the D-shape are adjacent one another, thereby creating a substantially circular, assembled cross-section as seen in FIG. 2. The D-shaped contour is formed by inserting a portion of the sub-cannulas between a pair of opposed dies and then closing the dies to deform the sub-cannulas and create the desired shape. The preferred embodiment of the dies are seen in FIGS. 4 and 5 and comprise an upper, convex die 52 and a lower, concave die 54. As seen in FIG. 4, a portion of the sub-cannula 14 is positioned between the opposed dies 52, 54. Next, the dies 52, 54 are closed, as seen in FIG. 5. The molding surface 60 of the concave lower die 54 is substantially complementary to the contour of the undeformed sub-cannula 14. Therefore, the portion of the sub-cannula received in this portion of the die retains substantially the same contour as prior to deformation. The molding surface 62 of the upper die 52 is preferably convex and deforms a portion of the reinforced sub-cannula 14 to deflect inwardly into the lumen 24 of the sub-cannula. The memory of the wire 30 utilized in the sub-cannula 14 is such that the convex portion 52 of the deformed sub-cannula will spring back to a substantially planar condition as seen in FIG. 2. In other words, in order to achieve the D-shaped contour of the sub-cannula 14 as seen in FIG. 2, it is preferred to use a convex die 52 to overcome the memory of the materials forming the reinforced sub-cannula. While experimentation has shown that it is preferred to use the combination of a convex and concave die, it may be possible to utilize a concave die and a substantially planar die, depending upon the selection of materials and the response of the materials to the deforming operation.

During conventional manufacturing operations, substantially the entire length of the first and second sub-cannulas are circular in cross-section prior to deformation in the dies 52, 54. As seen in FIG. 1, it is preferred that only an intermediate portion 64 of the first sub-cannula 14 is deformed into the D-shaped configuration, a body portion 65 distally from the D-shaped portion 64 remains circular in cross-section as does the body portion 66 proximately from the D-shaped portion 64. It is preferred that only a portion of the body adjacent the distal portion of the second sub-cannula 18 be deformed into the D-shaped configuration. The two deformed D-shaped portions are secured to one another by a conventional adhesive 56 to create the adhered portion 50 of the multi-lumen cannula 12. It is preferred that an adhesive be used which will fill any gaps in the adhered portion 50 to create a substantially smooth, exterior surface for the adhered portion 50.

The preferred embodiment of the adhesive used is known as Dymax 191 M adhesive which is manufactured by Dymax Corporation located in Torrington, Conn. This is a light curing adhesive which fills the gaps to create a smooth contour on the exterior surface of the multi-lumen cannula. Any adhesive which is essentially non-shrinking and preferably uses little or no evaporating solvents can be used.

The preferred embodiment of the multi-lumen cannula spaces the distal lumen apertures of the first and second sub-cannulas from one another. With this configuration, the multi-lumen cannula is ideally suited for use in a variety of cardiac surgical procedures which will be described in greater detail below. However, it is to be understood that the multi-lumen cannula 12 according to the invention can be adapted for a wide variety of applications and uses such that the proximal lumen apertures of the two sub-cannulas can be positioned immediately adjacent one another or spaced a variety of distances from one another. In addition, the multi-lumen cannula 12 according to the invention utilizes a pair of sub-cannulas which are D-shaped in cross-section. It is understood by persons skilled in the art that the multi-lumen cannula according to the invention can incorporate more than two sub-cannulas merely by changing the contour of the die and the adhered portion. For example, three or more wedge- or pie-shaped sub-cannulas can be mounted to one another according to the invention.

One key aspect of the preferred embodiment of the multi-lumen cannula according to the invention is the fact that reinforcement is provided in the septum 58 which separates the lumens of the two sub-cannulas. This reinforced septum provides significant advantages over previous multi-lumen cannulas because the cannula 12 can now accommodate dramatically different fluid pressure levels inside the immediately adjacent lumens. For example, significant positive fluid pressure can be created in one of the lumens while a significant negative fluid pressure is created in the adjacent lumen. Prior multi-lumen cannulas could not accommodate such varying pressure levels in adjacent lumens because the septum would deflect and quickly pinch closed the lower pressure lumen. The reinforced septum of the multi-lumen cannula according to the invention is a significant improvement in the art. In the preferred embodiment, each of the flat portions of the sub-cannulas are independently reinforced, resulting in a septum 58 which can resist deflection despite dramatically different fluid pressure levels in the adjacent lumens. However, it is understood that a multi-lumen cannula according to the invention could be constructed wherein only one of the several sub-cannulas is reinforced.

Figure 6:
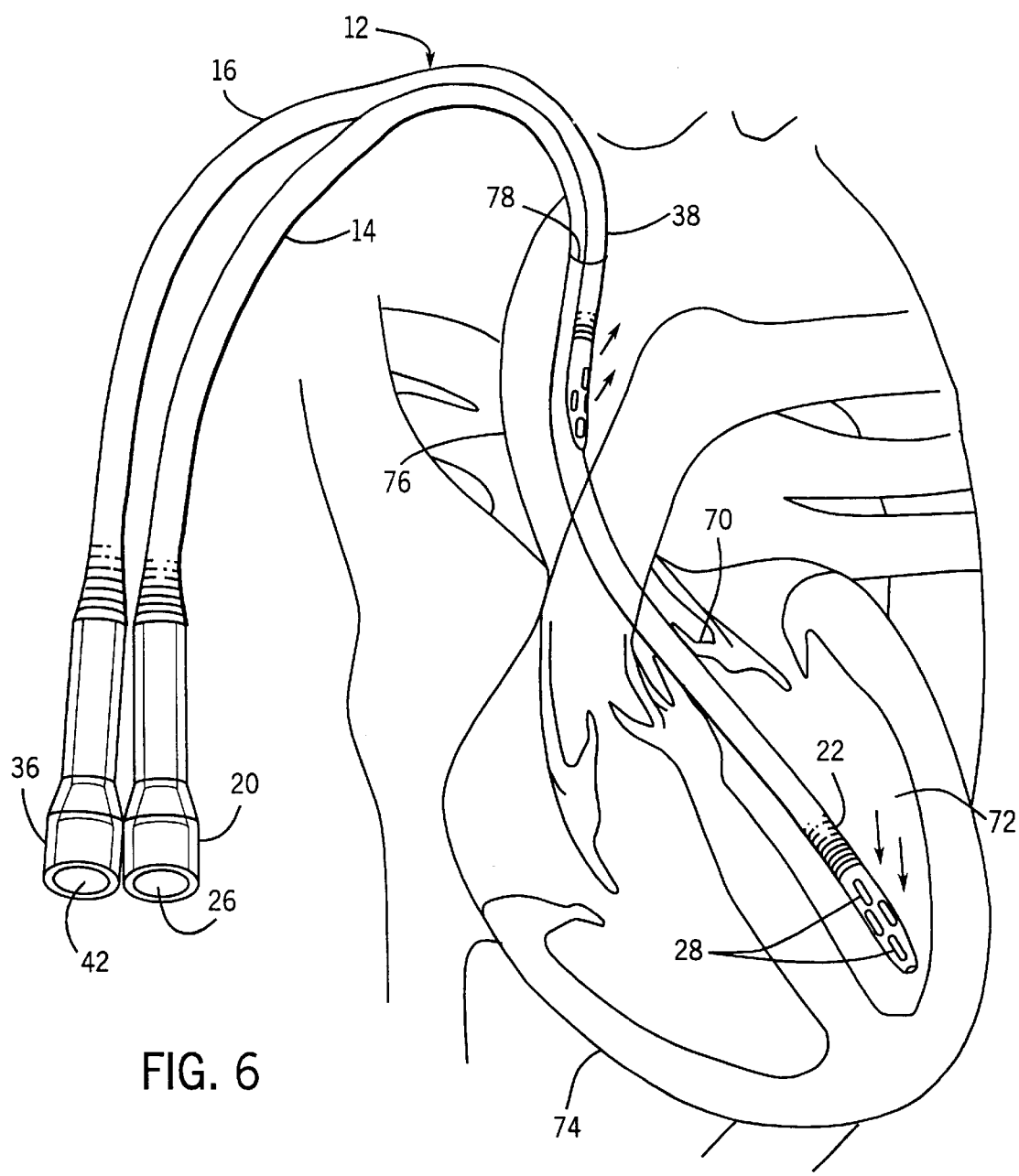
FIG. 6 is a schematic view of the multi-lumen cannula in a first operative position positioned in the human heart passing through the aortic valve.

The multi-lumen cannula 12 according to the invention, as seen in FIG. 1, can be used in a variety of applications to conduct fluid into and out of the human body. However, the lumen 12 is ideally suited for use in cardiac surgical procedures. As seen in FIG. 6, the cannula 12 can be used to conduct blood in a human vascular system across the aortic valve 70. In this first operative position, the distal lumen apertures 28 of the first sub-cannula 14 are positioned in the left ventricle 72 of the heart 74, and the distal lumen apertures 44 of the second sub-cannula 16 are positioned in the aorta 76 downstream from the aortic valve 70. With this structure and position, a single incision 78 is formed in the aorta to accommodate the fluid flow paths for withdrawing blood from the left ventricle and simultaneously supplying blood to the aorta 76. Previously, two incisions were required to accomplish both of these functions. The fluid withdrawn from the left ventricle through the first sub-cannula 14 will likely be at a lower fluid pressure than the blood supplied to the aorta 76 through the second sub-cannula 16. The reinforced septum 58 can accommodate these differing fluid pressures without deforming and altering the cross-sectional area of the lumens 24, 40.

In the first operative position as seen in FIG. 6, the proximal end 20 of the first sub-cannula 14 is fluidly connected to a pump or some other mechanism for withdrawing blood from the left ventricle 72, and the proximal end 36 of the second sub-cannula 16 is fluidly connected to the outlet of this pump.

Figure 7:
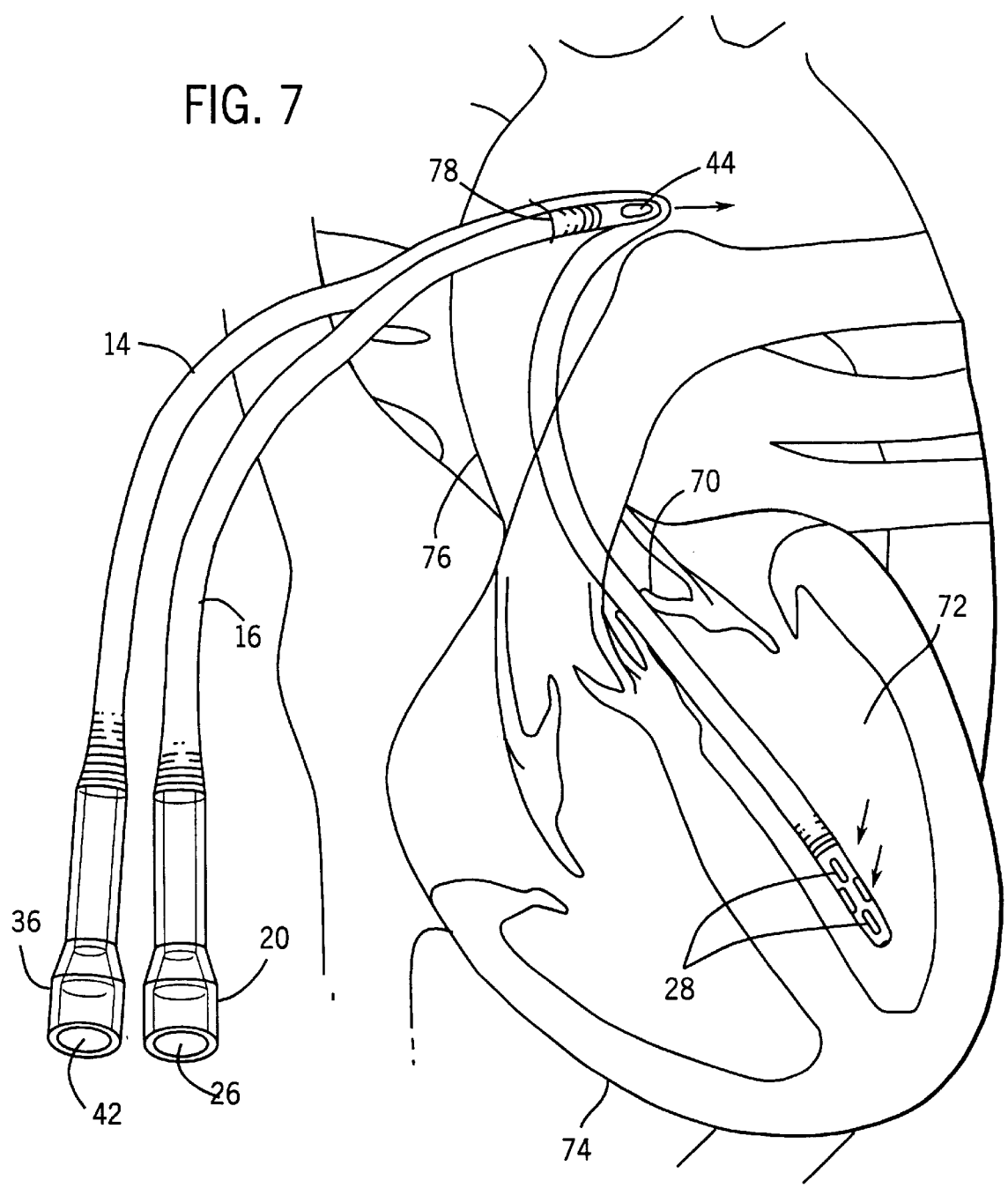
FIG. 7 is a schematic view of the multi-lumen cannula in a second operative position positioned in the human heart passing through the aortic valve.

FIG. 7 shows the multi-lumen cannula 12 according to the invention in a second operative position. Similar to the positioning shown in FIG. 6, the distal lumen apertures 28, 42 of the sub-cannulas 14, 16 are positioned on opposite sides of the aortic valve 70. However, the incision 78 has been repositioned on the aorta 76 closer to the valve 70.

Figure 8:
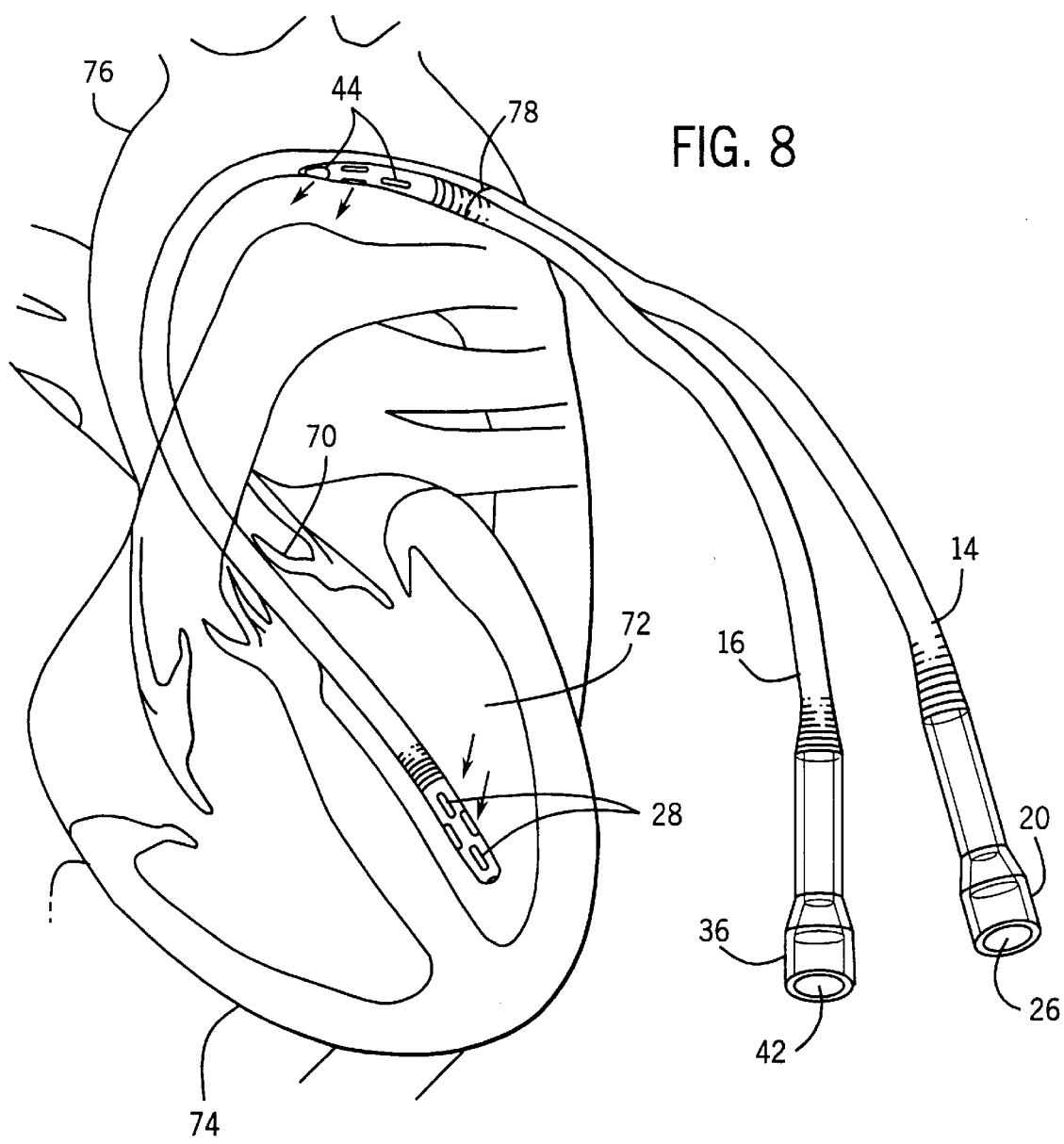
FIG. 8 is a schematic view of the multi-lumen cannula in a third operative position positioned in the human heart passing through the aortic valve.

FIG. 8 is a schematic drawing of a third operative position for the multi-lumen cannula 12 according to the invention. Similar to the positions seen in FIGS. 6 and 7, the distal lumen apertures 28,42 are positioned on opposite sides of the aortic valve and the incision 78 has been positioned further downstream from the earlier applications.

Figure 9:
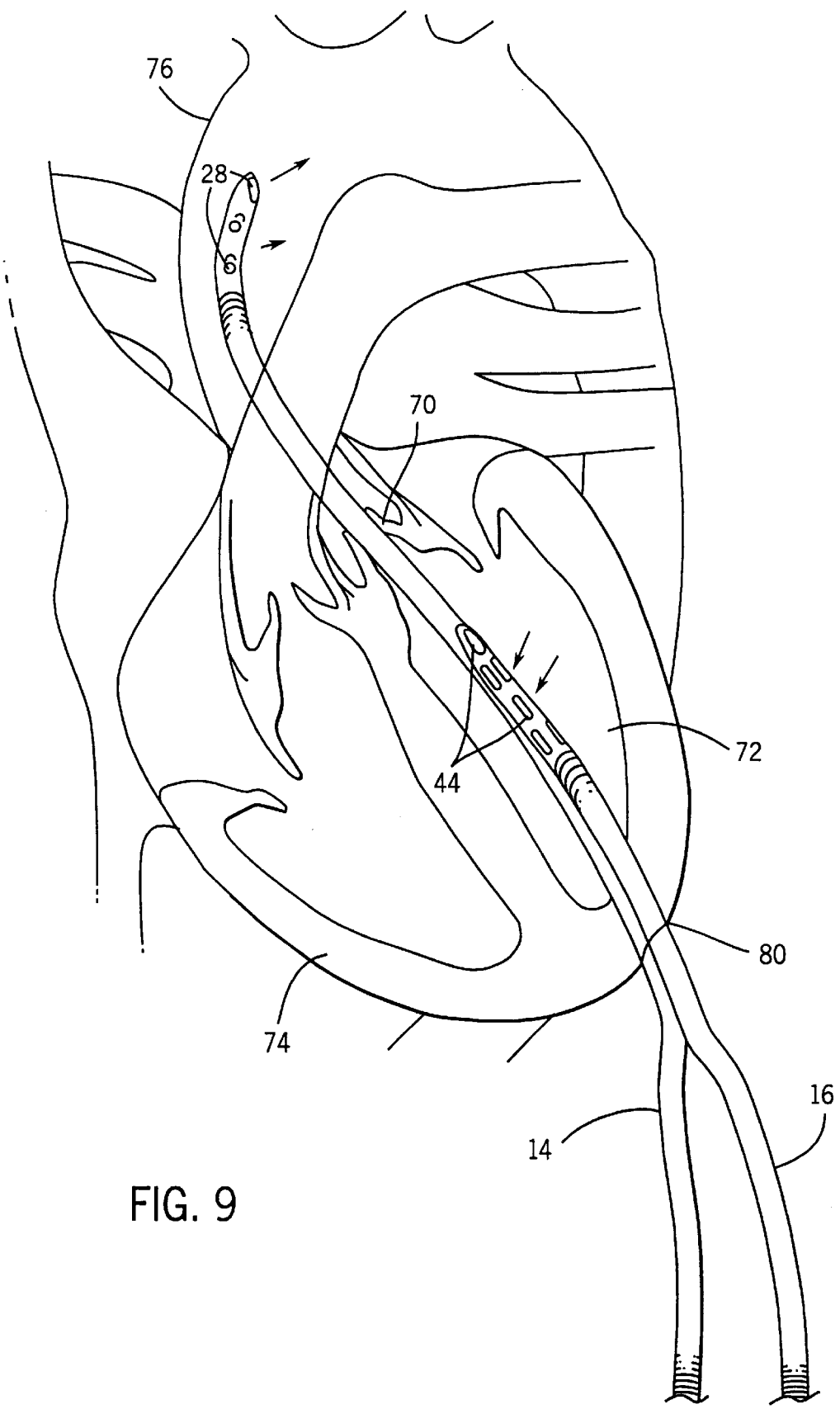
FIG. 9 is a schematic view of the multi-lumen cannula in a fourth operative position positioned in the human heart passing through the aortic valve.

FIG. 9 shows the multi-lumen cannula 12 in a fourth operative position which, similar to the earlier operative positions, shows the distal lumen apertures 28, 42 on opposite sides of the aortic valve 70. However, in this position, the cannula 12 is inserted through an incision 80 formed directly in the wall of the left ventricle 72. In this position, blood is withdrawn from the left ventricle 72 through the distal lumen aperture 44 of the second sub-cannula 16, and the blood is discharged into the aorta 76 through the distal lumen aperture 28 of the first sub-cannula 14. As is evident from the various applications seen in FIGS. 6–9, the preferred embodiment of the multi-lumen cannula according to the invention is ideally suited to provide left-heart assist.

Figure 10:
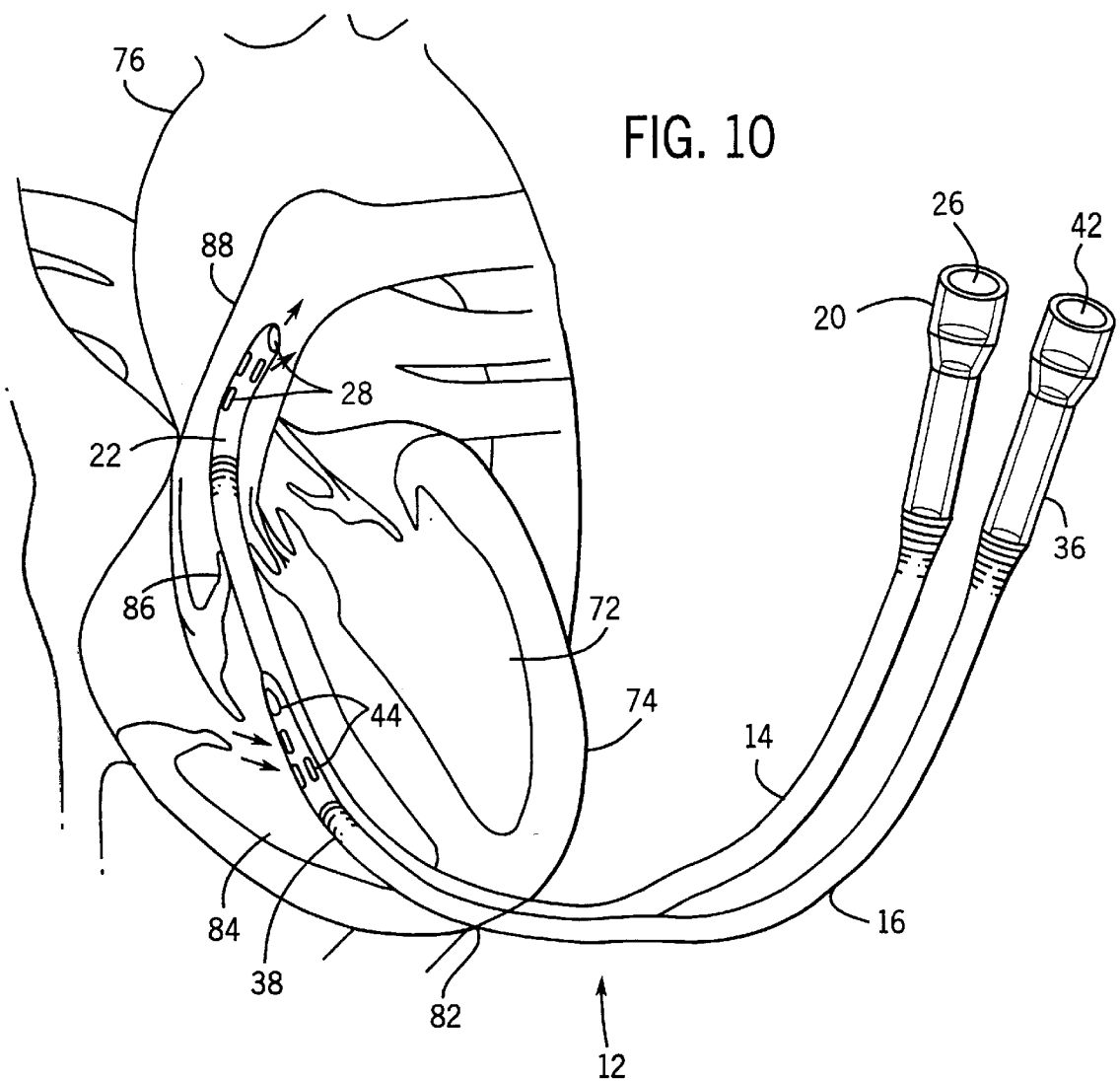
FIG. 10 is a schematic view of the multi-lumen cannula in a fifth operative position positioned in the human heart passing through the pulmonary valve.
Figure 11:
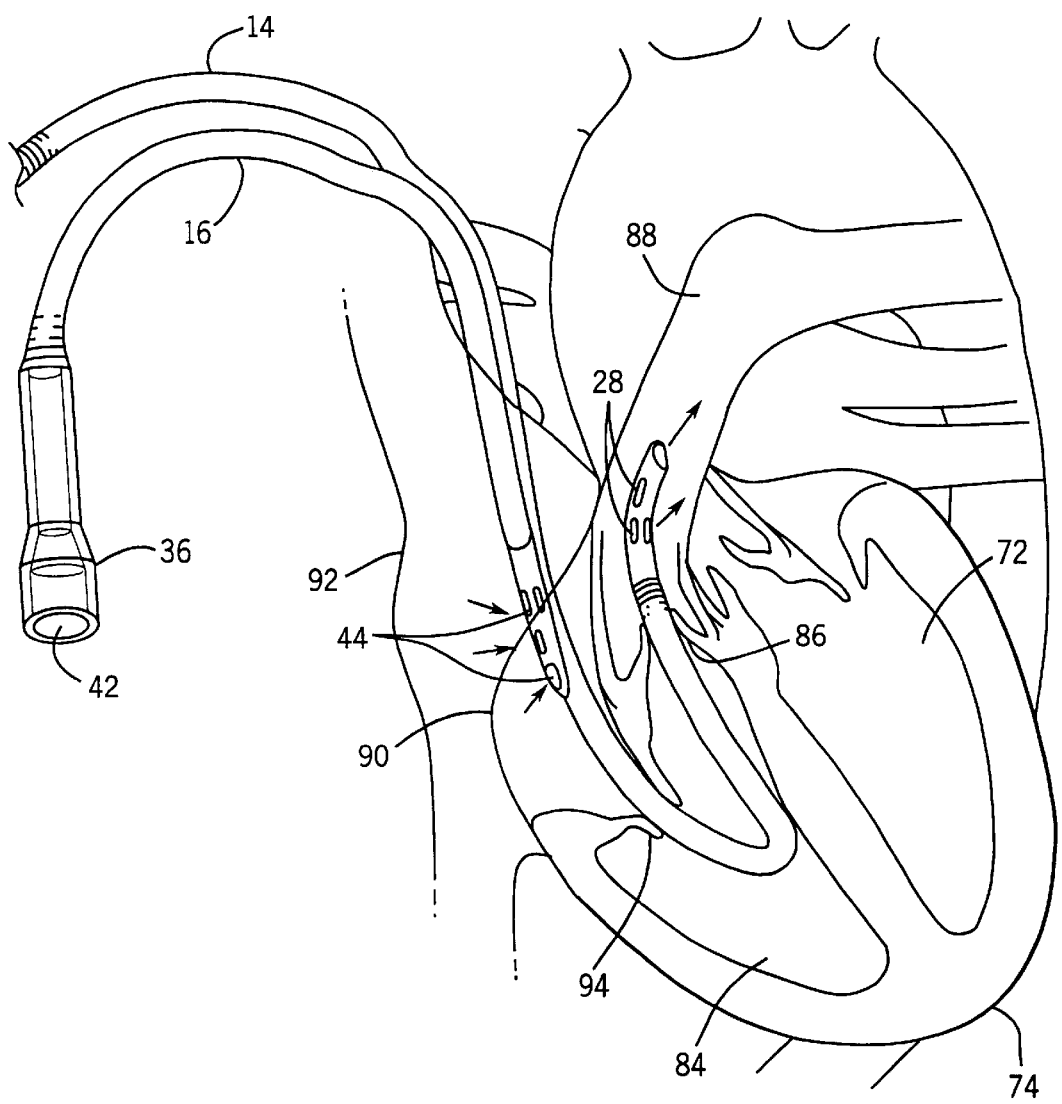
FIG. 11 is a schematic view of the multi-lumen cannula in a sixth operative position positioned in the human heart passing through both the tricuspid valve and pulmonary valve.

FIGS. 10 and 11 show use of the multi-lumen cannula 12 according to the invention for right-heart assist procedures. As seen in FIG. 10, the multi-lumen cannula 12 has been inserted into the heart 74 through an incision 82 formed in the wall of the right ventricle 84. The distal lumen apertures 44 of the second sub-cannula 16 are positioned in the right ventricle 84 while the distal lumen apertures 28 of the first sub-cannula 14 are positioned on the other side of the pulmonary valve 86 in the pulmonary artery 88. In this operative position, the distal end 38 of the second sub-cannula 16 is fluidly connected to the inlet of a pump, and the distal end 22 of the first sub-cannula 14 is fluidly connected to the outlet of the pump (not shown).

FIG. 11 shows use of the multi-lumen cannula 12 according to the invention in a sixth operative position. In this position, the cannula is inserted through an incision (not shown) formed in one of the right atrium 90 or the vena cava 92. The cannula is inserted past the tricuspid valve 94, through the right ventricle 84, past the pulmonary valve 86, and into the pulmonary artery 88. In this position, the blood is withdrawn from the right atrium 90 and vena cava 92 through the distal lumen apertures 44 of the second sub-cannula 16 and the blood is discharged into the pulmonary artery 88 through the distal lumen apertures 28 of the first sub-cannula 14. The distal ends of the first and second sub-cannulas 14, 16 are preferably connected to a fluid pump (not shown) to accommodate this movement of the blood in the vascular system.

FIGS. 10 and 11 show two alternative positions of the multi-lumen cannula 12 according to the invention to provide right-heart assist. It is to be understood that two different multi-lumen cannulas 12 according to the invention can be used simultaneously to provide both right and left-heart assist functions. For example, a first multi-lumen cannula can be positioned in one of the positions seen in FIGS. 6–9 to provide left-heart assist while a second multi-lumen cannula according to the invention can be positioned as seen in one of FIGS. 10 and 11 to provide right-heart assist. Each use of the multi-lumen cannula 12 according to the invention as described above provides an advantage over the prior art by eliminating an incision in the vasculature system which, in view of the significant fluid pressures inside the system, can be a dramatic improvement over the past procedures. In addition, a single, multi-lumen cannula can be used to accommodate dramatically different fluid pressures within each of the lumens without undesirable deforming or altering the cross-sectional area of the lumens.

Figure 12:
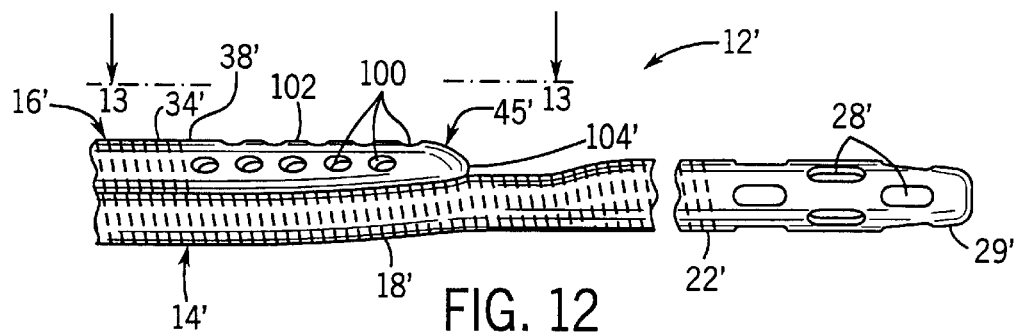
FIG. 12 is a partial, top plan view of a second embodiment of a multi-lumen cannula showing a second sub-cannula with a reverse flow tip.
Figure 13:
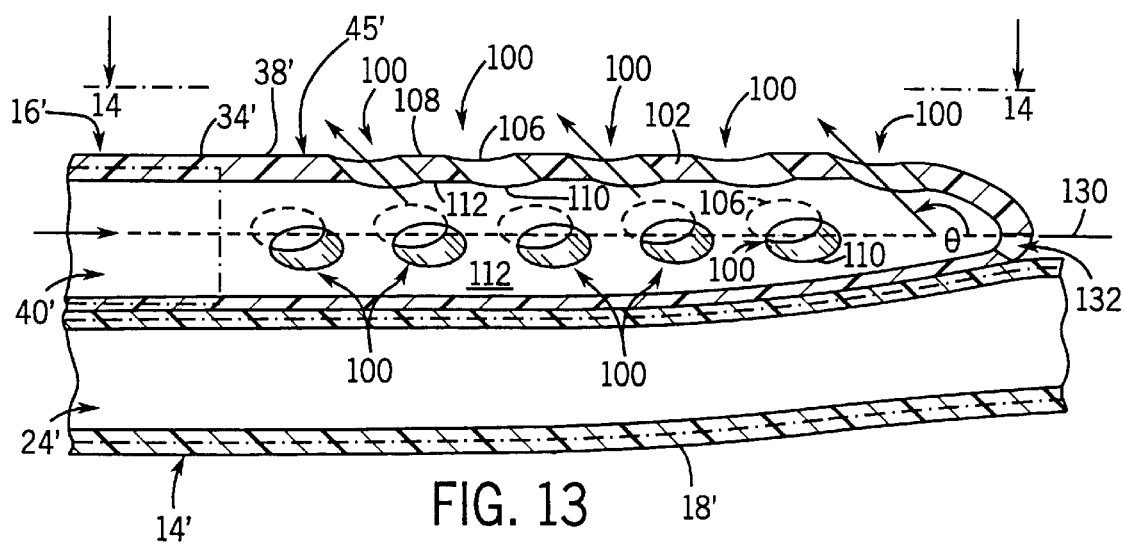
FIG. 13 is a cross-sectional view of taken generally along the line 13—13 of FIG. 12.
Figure 14:
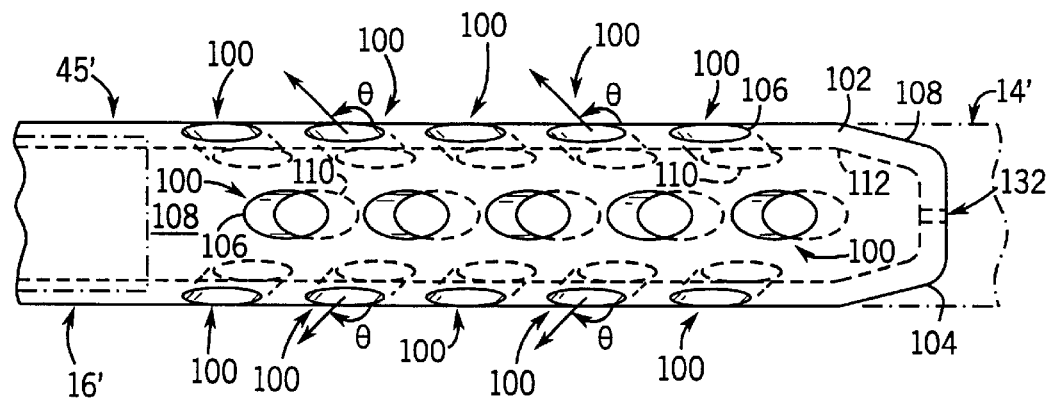
FIG. 14 is sectional view taken generally along the line 14—14 of FIG. 13.

Referring now to FIGS. 12–14, a second embodiment of a multi-lumen cannula 12' is shown. The multi-lumen cannula 12' is similar to the multi-lumen cannula 12 of FIG. 1. For purposes of simplicity, like parts of the multi-lumen cannulas 12, 12' will be identified by like reference numerals. The multi-lumen cannula 12' includes a first sub-cannula 14' and a second sub-cannula 16'. Each of the first and second sub-cannulas 14', 16' includes a body portion 18', 34' having a proximal end (not shown), a distal end 22', 38', and a cannula tip 29', 45' coupled to the distal end 22', 38'. In the first sub-cannula 14', a lumen 24' extends from a proximal lumen aperture (not shown) provided in the proximal end to at least one distal lumen aperture 28' formed in the cannula tip 29' at the distal end 22'.

The second sub-cannula 16' includes a lumen 40' which extends from a proximal lumen aperture (not shown) to at least one fluid outlet 100 formed in a side wall 102 of the cannula tip 45'. The cannula tip 45' is a reverse flow tip which preferably has a plurality of fluid outlets 100 and a substantially closed distal end 104. The fluid outlets 100 are formed in a sector of the cannula tip 45'. The fluid outlets 100 have a configuration that is different from the distal lumen apertures 44 of the multi-lumen cannula 12. The fluid outlets 100 extend toward the proximal end and are configured to reverse the flow of fluid exiting the second sub-cannula 16'. Each fluid outlet 100 includes an opening 106, formed in an exterior surface 108 of the side wall 102, and an opening 110 formed in an interior surface 112 of the side wall 102. The exterior surface opening 106 of each fluid outlet 100 is located proximally of the interior surface opening 110. As will be described in greater detail below, the fluid, which enters the second sub-cannula 16' through the proximal lumen aperture 42' and flows through the lumen 40', will exit the cannula tip 45' in a direction generally opposite to the original direction of flow.

The fluid outlets 100 of cannula tip 45' are advantageous, as they minimize trauma to the heart and vessels leading to and from the heart caused by pressurized fluid exiting the cannula tip 45'. For example, in a cardiac surgical procedure such as that shown in FIG. 6, the fluid outlets 100 of the second sub-cannula 16', the tip of which is inserted downstream of the aorta 76, will direct fluid exiting the second sub-cannula 16' away from the aortic valve 70 as well as away from the walls of the aorta 76. Since the fluid outlets 100 reverse the flow of fluid and direct it backwards, the fluid outlets 100 decrease the fluid pressure on the aortic valve 70 and walls of the aorta 76. The decreased fluid pressure on the vessel walls reduces the possibility that plaque or blood clots may become dislodged from the vessel walls, thereby minimizing the risk of embolic complications.

Figure 15:
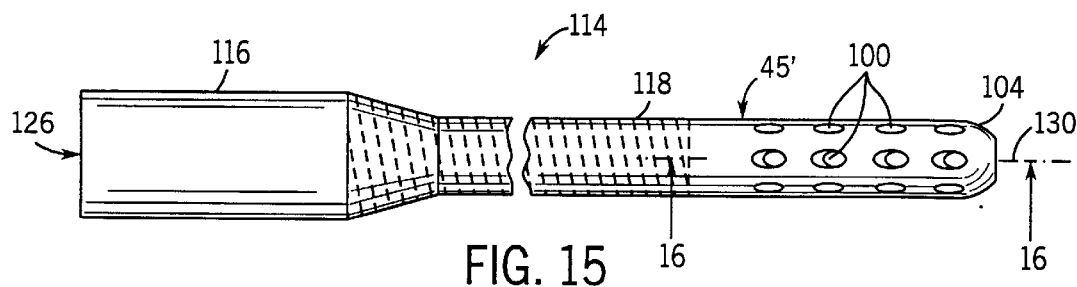
FIG. 15 is a partial top plan view of a single-lumen cannula, according to the invention, having a reverse flow tip.
Figure 16:
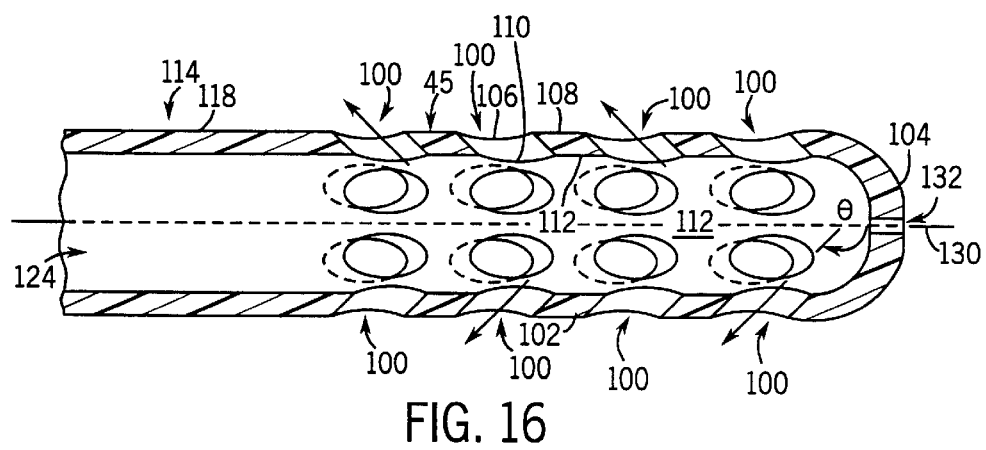
FIG. 16 is a cross-sectional view taken generally along the line 16—16 of FIG. 15.

As illustrated in FIGS. 15 and 16, a cannula tip with a plurality of reverse flow fluid outlets, such as the cannula tip 45', may also be provided on a single-lumen cannula 114. The cannula 114 has a proximal end 116, a distal end 118, and a cannula tip 45' coupled to the distal end 118 and including a substantially closed distal end 104. A lumen 124 extends between a proximal lumen aperture 126 provided in the proximal end 116 and at least one fluid outlet 100 formed in a side wall 102 of the cannula tip 45'. The fluid outlets 100 extend toward the proximal end 116 and reverse the flow of fluid exiting from the cannula tip 45'.

The details of the fluid outlets 100 for the multi-lumen cannula 12' and the single-lumen cannula 114 are best shown in FIGS. 13, 14 and 16. Each fluid outlet 100 includes an opening 106 formed in an exterior surface 108 of the side wall 102 and an opening 110 formed in an interior surface 112 of the side wall 102, with the exterior surface opening 106 located proximally of the interior surface opening 110. Each fluid outlet 100 is positioned at an obtuse angle Θ with respect to a longitudinal axis 130 of the cannula tip 45'. The optimal angle Θ for each fluid outlet 100 is preferably between 135° and 165°, however, any angle between 105° and 175° may be selected.

In operation, fluid flows through the lumen of the multi-or single-lumen cannula 12', 114 from the proximal end to the cannula tip 45' at the distal end 22', 118. When the fluid reaches the substantially closed distal end 104 of the cannula tip 45', it is re-directed toward the proximal end and exits through the fluid outlets 100 at the angle Θ into the receiving chamber of the heart or vessel. While the substantially closed distal end 104 of the cannula tip 45' prevents fluid from exiting therethrough, a tiny aperture is provided to prevent air from becoming entrapped in the distal end of the cannula tip 45'.

The multi- and single-lumen cannulas 12', 114 with the reverse flow fluid outlets 100 are primarily applicable to arterial cannulas or cannulas used for retrograde cardioplegia solution perfusion. The number and size of the fluid outlets 100 provided on the cannula tip 45' is dependent on the desired flow rate and fluid pressure. Given the angle Θ, the fluid outlets 100 are preferably disposed about the cannula tip 45' such that the exterior surface opening 106 of a first fluid outlet 100 does not overlap the interior surface opening 110 of any adjacent fluid outlet 100. However, it is also foreseeable that the exterior surface opening 106 of one fluid outlet 100 may overlap the interior surface opening 110 of an adjacent fluid outlet 100 by as much as 50%.

Figure 17:
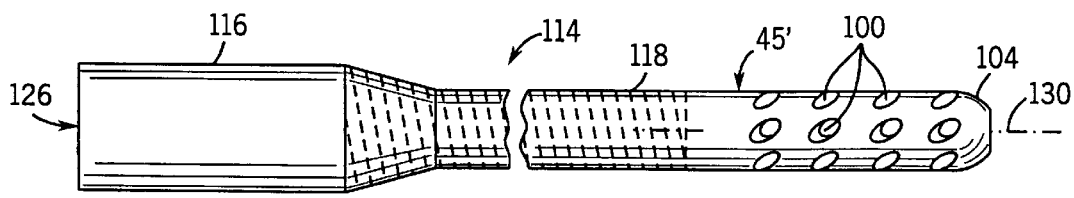
FIG. 17 is an alternate embodiment of the cannula reverse flow tip, showing fluid outlets that are non-parallel to a longitudinal axis of the cannula tip.
Figure 18:
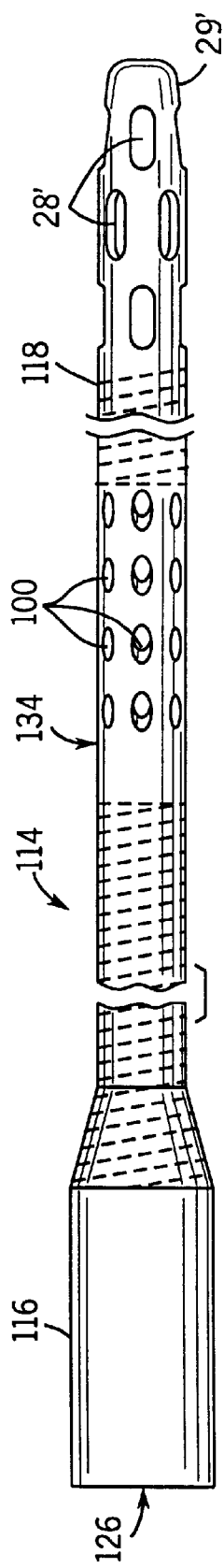
FIG. 18 is a partial top plan view of a single-lumen cannula including a plurality of reverse flow fluid outlets disposed about a mid-section of the cannula.

In the preferred embodiment of the cannulas 12', 114 shown in FIGS. 12–16, the fluid outlets 100 extend along and are substantially parallel to the longitudinal axis 130 of the cannula tip 45'. One skilled in the art will appreciate that it is also within the scope of the invention for at least a portion of the fluid outlets 100 to be non-parallel to the longitudinal axis 130. As illustrated in FIGS. 17 and 18, the fluid outlets 100 may spiral about or twist with respect to the longitudinal axis 130.

The fluid outlets 100 are spaced about at least a sector of the cannula tip 45'. The single-lumen cannula 114 has fluid outlets 100 disposed equally about the entire cannula tip 45'. However, the fluid outlets 100 may be disposed in only a sector less than the entire cannula tip 45'. As illustrated in the second sub-cannula 16' of the multi-lumen cannula 12', the fluid outlets 100 are disposed about a 180° sector, or half, of the cannula tip 45'. It is understood by those skilled in the art that the sector about which the fluid outlets 100 are disposed may be increased or decreased, depending on the desired need.

One inherent result achieved by providing fluid outlets 100 on a sector of the cannula tip 45', which is less than the entire tip, is steerability of the single-lumen cannula 114. For example, in a cannula having fluid outlets disposed about half (i.e., a 180° sector), or less than half, of the cannula tip, fluid flowing through the lumen of the cannula and exiting the cannula tip will steer the cannula tip in a direction away from the side with the fluid outlets. It should be noted that steerability of the single-lumen cannula 114 may also be accomplished by providing an unbalanced amount of fluid outlets 100 about the cannula tip 45', thereby concentrating a number of the fluid outlets 100 in a sector of the cannula tip 45'.

Figure 19:
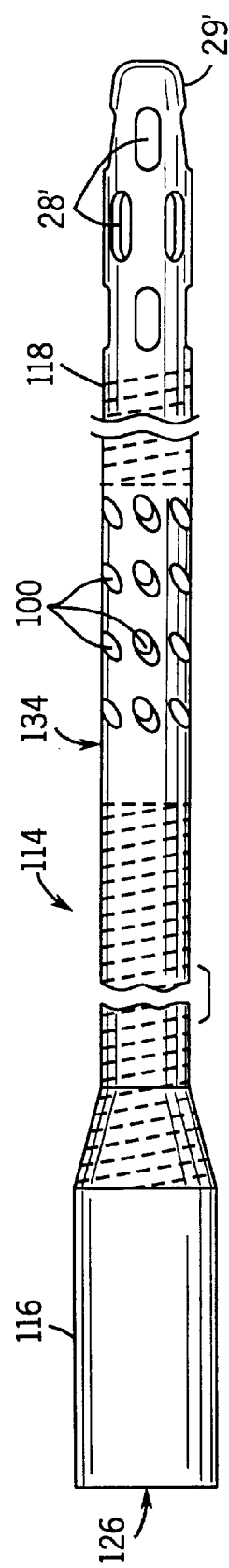
FIG. 19 is an alternate embodiment of the cannula of FIG. 19, showing reverse flow fluid outlets that are non-parallel to a longitudinal axis of the cannula.

While it is preferred that the fluid outlets 100 are provided in the cannula tip 45', the fluid outlets 100 may also be provided elsewhere along the cannula. As illustrated in FIGS. 18 and 19, the single-lumen cannula 114 has a cannula tip 29', identical to that of the second sub-cannulas 16, 16' of multi-lumen cannulas 12, 12' and including normal distal lumen apertures 28'. The cannula 114 also includes a plurality of fluid outlets 100 formed in a mid-section 134 of the cannula. The fluid outlets 100 in the mid-section 134 reverse the flow of fluid which exits the lumen 124. The fluid outlets 100 may be substantially parallel to a longitudinal axis of the cannula 114 (FIG. 18) or may spiral or twist thereabout (FIG. 19).

Figure 20:
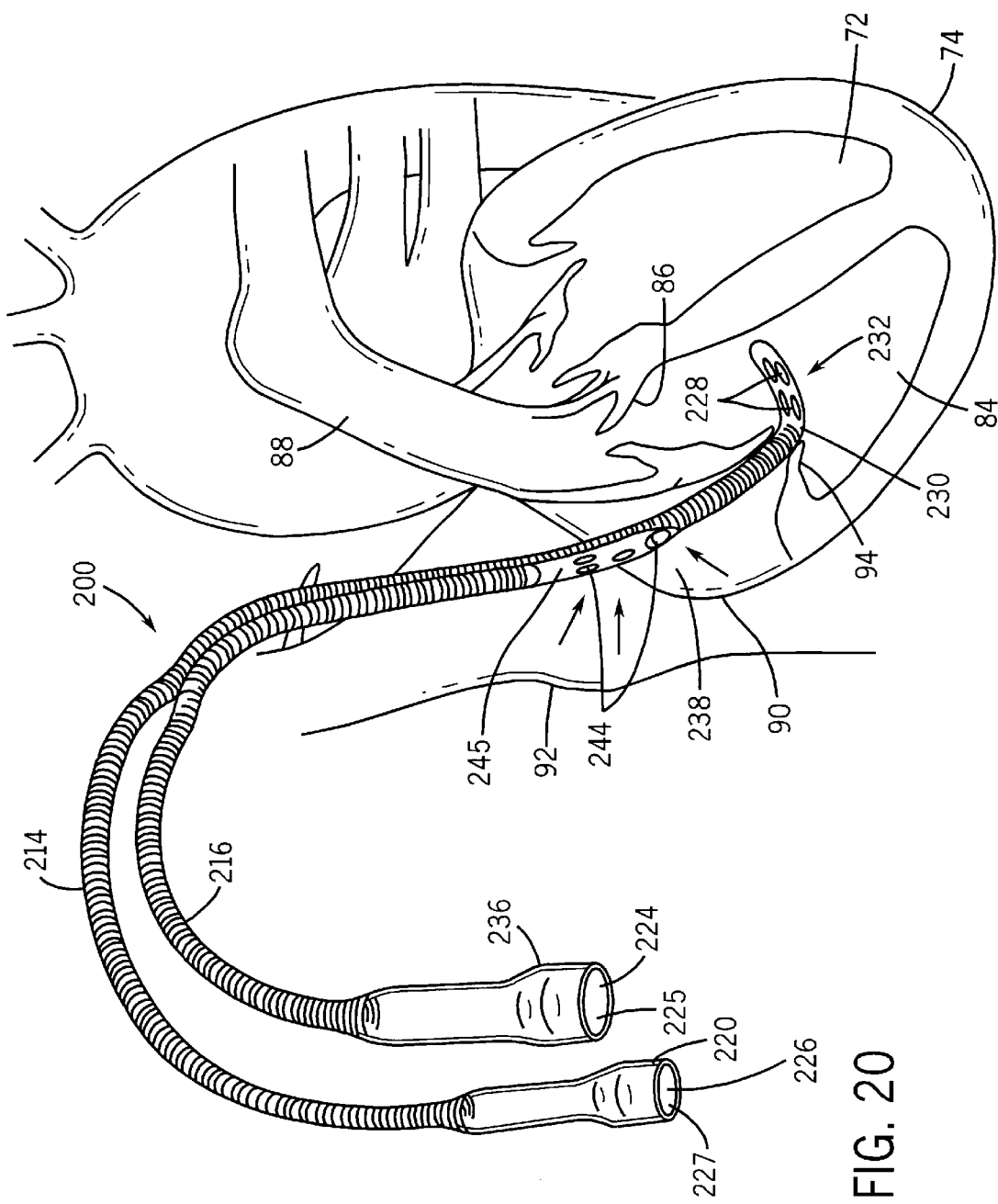
FIG. 20 is an alternate embodiment of the multi-lumen cannula, having a bent tip, and positioned with the distal end in the right ventricle.

Referring now to FIG. 20, a multi-lumen cannula 200 is depicted. Multi-lumen cannula 200 includes a first sub-cannula 214 and a second sub-cannula 216 which are mounted to one another to create multi-lumen cannula 200. Multi-lumen cannula 200 has a first sub-cannula 214 with a lumen 226 extending from a proximal lumen aperture 227 provided on the proximal end 220 to at least one distal lumen aperture 228 formed in cannula tip 230 at the distal end 232. A second sub-cannula 216 is substantially identical to the first sub-cannula 214 and includes a proximal end 245, a distal end 238, a lumen 224, a proximal lumen aperture 225, and at least one distal lumen aperture 244 formed in a cannula tip 245.

FIG. 20 depicts multi-lumen cannula 200 in a seventh operative position, according to one embodiment of the invention. According to the operative position shown, distal lumen apertures 244 and 228 are shown on opposite sides of tricuspid valve 94. The cannula is inserted through vena cava 92 (inferior vena cava or superior vena cava) or is inserted through the wall of right atrium 90. Distal tip 230 is inserted past tricuspid valve 94 and into right ventricle 84. In this position, the blood or fluid is withdrawn from vena cava 92 or alternatively from right atrium 90 through distal lumen apertures 244 of second sub-cannula 216 and the blood or fluid is discharged into right ventricle 84 through distal lumen apertures 228 of first sub-cannula 214. The distal ends of the first and second sub-cannulas 214 and 216 are preferably connected to a fluid pump (not shown) to accommodate the movement of blood in the vascular system.

The placement of multi-lumen cannula 200 depicted in FIG. 20 provides hemodynamic stability of the right ventricle, such that during surgery when the heart is lifted or manipulated, the right ventricle is not substantially compressed thereby reducing the volume of the ventricle and the amount of blood that the ventricle is able to pump. In other words, the placement of multi-lumen cannula 200 depicted in FIG. 20 may be used to maintain the volume of the right ventricle at a substantially constant volume. The blood collected from the right atrium (or superior vena cava and inferior vena cava) is pumped into the right ventricle using multi-lumen cannula 200.

To further assist insertion of distal tip 230 though tricuspid valve 94 and into right ventricle 84, distal tip 230 is bent at an angle relative to distal tip 245. In other words, distal tip 230 may be defined by a first axis and distal tip 245 may be defined by a second axis, the first axis and the second axis are not aligned, forming a bent tip 245. (Alternatively, distal tip 245 may be at least partially curved, thereby facilitating insertion.) The bent angle of distal tip 230 facilitates insertion though tricuspid valve 94. Alternatively, tip 230 may not necessarily be bent or tip 230 may have differing flexural properties than other portions of multi-lumen cannula 200. Therefore, multi-lumen cannula 200 is used to pressurize right ventricle 84 by pumping blood from right atrium 90 (or alternatively vena cava 92) and therefore pressurizing blood into pulmonary artery 88 through pulmonary valve 86.

Reasonable variation and modification are possible within the spirit of the foregoing specification and drawings without departing from the scope of the invention.

What is claimed is:

1. A method of pressurizing the right ventricle of the heart, the method comprising:

providing a multi-lumen cannula comprising:
a first sub-cannula including a proximal end, a distal end, a lumen extending between the proximal and distal ends, and proximal and distal fluid apertures formed in the lumen; and
a second sub-cannula including a proximal end, a distal end, a lumen extending between the proximal and distal ends, and proximal and distal fluid apertures formed in a lumen, wherein the distal fluid apertures of the two lumens are spaced from one another along the axial length of the multi-lumen cannula;

inserting the cannula into the vasculature system of a patient so that the distal fluid aperture of the lumen of the second sub-cannula is received in one of the right atrium, the superior vena cava, and the inferior vena cava, and the distal fluid aperture of the lumen of the first sub-cannula is received in the right ventricle; and fluidly connecting the proximal fluid apertures of the first and second sub-cannulas to a fluid conducting pump for moving fluid through the two sub-cannulas.

2. The method of pressurizing the right ventricle of the heart according to claim 1 wherein the cannula is inserted into the vasculature system through an incision formed in the superior vena cava.

3. The method of pressurizing the right ventricle of the heart according to claim 1 wherein the cannula is inserted into the vasculature system through an incision formed in the inferior vena cava.

4. The method of pressurizing the right ventricle of the heart according to claim 1 wherein the cannula is inserted into the vasculature system through an incision formed in the right atrium.

5. The method of pressurizing the right ventricle of the heart according to claim 1 wherein the distal end of the lumen of the first sub-cannula is on a first sub-cannula tip having a first axis, the distal end of the second sub-cannula is on a second sub-cannula tip having a second axis, and the first axis and second axis are not aligned.

6. A method of pressurizing the right ventricle of the heart according to claim 1 wherein the cannula is inserted through the tricuspid valve of the heart, and substantially forms a seal with the tricuspid value.

7. A method of pressurizing the right ventricle of the heart according to claim 1 wherein the distal fluid apertures of the first sub-cannula are directed toward the proximal end of the first sub-cannula body to direct the flow of fluid entering the cannula.

8. The method of pressurizing the right ventricle of the heart according to claim 1 wherein the bent tip is inserted through the tricuspid valve.

9. The method of pressurizing the right ventricle of the heart according to claim 1 wherein the fluid from the distal tip of the first sub-cannula is pumped into the pulmonary artery through the right ventricle.

10. The method of pressurizing the right ventricle of the heart according to claim 1 whereby hemodynamic stability of the right ventricle is substantially maintained.

11. The method of pressurizing the right ventricle of the heart according to claim 1 wherein the volume of the right ventricle is substantially maintained.

12. The method of pressurizing the right ventricle of the heart according to claim 1 wherein a portion of the first sub-cannula is circular in cross section and another portion of the first sub-cannula is non-circular, a portion of the second sub-cannula is circular in cross section and another portion of the second sub-cannula is non-circular, and the non-circular portion of the first sub-cannula is adhered to the non-circular portion of the second sub-cannula so that the cross section of the adhered portions of the first and second sub-cannulas is substantially circular.

13. A method of placing a cannula into the heart, the method comprising:
    providing a multi-lumen cannula comprising:
        a first sub-cannula including a proximal end, a distal end, a lumen extending between the proximal and distal ends, and proximal and distal fluid apertures formed in the lumen; and
        a second sub-cannula comprising a proximal end, a distal end, a lumen extending between the proximal and distal ends, and proximal and distal fluid apertures formed in the lumen, wherein the distal fluid apertures of the two lumens are spaced from one another along the axial length of the multi-lumen cannula and the distal tip of the first sub-cannula having a first axis, the distal end of the second sub-cannula is on a second sub-cannula tip having a second axis, and the first axis and second axis are not aligned;
    inserting the cannula into the vasculature system of a patient so that the distal fluid aperture of the lumen of the second sub-cannula is received in one of the right atrium, the superior vena cava, and the inferior vena cava; and
    fluidly connecting the proximal fluid apertures of the first and second sub-cannulas to a fluid conducting pump for moving fluid through the two sub-cannulas.

14. The method of pressurizing the right ventricle of the heart according to claim 13 wherein the cannula is inserted into the vasculature system through an incision formed in the superior vena cava.

15. The method of pressurizing the right ventricle of the heart according to claim 13 wherein the cannula is inserted into the vasculature system through an incision formed in the inferior vena cava.

16. The method of pressurizing the right ventricle of the heart according to claim 13 wherein the cannula is inserted into the vasculature system through an incision formed in the right atrium.

17. A method of pressurizing the right ventricle of the heart according to claim 13 wherein the cannula is inserted through the tricuspid valve of the heart, and substantially forms a seal with the tricuspid value.

18. A method of pressurizing the right ventricle of the heart according to claim 13 wherein the distal fluid apertures of the first sub-cannula are directed toward the proximal end of the first sub-cannula body to direct the flow of fluid entering the sub-cannula.

19. A method of pressurizing the right ventricle of the heart, the method comprising:
    providing a multi-lumen cannula comprising:
        a first sub-cannula including a proximal end, a distal end, a lumen extending between the proximal and distal ends, and proximal and distal fluid apertures formed in the lumen, a portion of the first sub-cannula being circular in cross section and another portion being non-circular; and
        a second sub-cannula including a proximal end, a distal end, a lumen extending between the proximal and distal ends, and proximal and distal fluid apertures formed in a lumen, a portion of the sub-cannula being circular in cross section and another portion being non-circular, wherein the distal fluid apertures of the two lumens are spaced from one another along the axial length of the multi-lumen cannula and the non-circular portion of the first sub-cannula is adhered to the non-circular portion of the second sub-cannula so that the cross section of the adhered portions of the first and second sub-cannulas is substantially circular;
    inserting the cannula into the vasculature system of a patient so that the distal fluid aperture of the lumen of the first sub-cannula is received in one of the right atrium, the superior vena cava, and the inferior vena cava, and the distal fluid aperture of the lumen of the second sub-cannula is received in the right ventricle;
    fluidly connecting the proximal fluid apertures of the first and second sub-cannulas to a fluid conducting pump for moving fluid through the two sub-cannulas from one of the right atrium, the superior vena cava, and the inferior vena cava to the right ventricle.

20. The method of pressurizing the right ventricle of claim 19 wherein the distal tip of the second sub-cannula is not substantially axially aligned with the distal tip of the first sub-cannula.

21. The method of pressurizing the right ventricle of claim 19 whereby hemodynamic stability of the right ventricle is substantially maintained.

* * * * *

UNITED STATES PATENT AND TRADEMARK OFFICE
CERTIFICATE OF CORRECTION

PATENT NO. : 6,264,645 B1
DATED : July 24, 2001
INVENTOR(S) : Jonkman

Page 1 of 1

It is certified that error appears in the above-identified patent and that said Letters Patent is hereby corrected as shown below:

<u>Column 11, claim 6,</u>
Line 7, please delete "tricuspid value" and replace it with -- tricuspid valve --.

<u>Column 12, claim 17,</u>
Line 14, please delete "tricuspid value" and replace it with -- tricuspid valve --.

Signed and Sealed this

Twenty-fifth Day of December, 2001

Attest:

*Attesting Officer*

JAMES E. ROGAN
*Director of the United States Patent and Trademark Office*